(12) United States Patent
Misiakos et al.

(10) Patent No.: US 7,319,046 B2
(45) Date of Patent: Jan. 15, 2008

(54) INTEGRATED OPTOELECTRONIC SILICON BIOSENSOR FOR THE DETECTION OF BIOMOLECULES LABELED WITH CHROMOPHORE GROUPS OR NANOPARTICLES

(75) Inventors: Konstantinos Misiakos, Institute of Microelectronics, NCSR Demokritos, Aghia Paraskevi (GR) 153 10; Sotirios Kakabakos, Institute of Radioisotopes and Radiodiagnostic Products, NCSR Demokritos, Aghia Paraskevi (GR) 153 10

(73) Assignees: Konstantinos Misiakos, Attiki (GR); Sotirios Kakabakos, Attiki (GR); National Centre for Scientific Research Demkritos, Attiki (GR)

( * ) Notice: Subject to any disclaimer, the term of this patent is extended or adjusted under 35 U.S.C. 154(b) by 193 days.

(21) Appl. No.: 10/496,099

(22) PCT Filed: Nov. 29, 2002

(86) PCT No.: PCT/GR02/00061
§ 371 (c)(1),
(2), (4) Date: May 18, 2004

(87) PCT Pub. No.: WO03/046527
PCT Pub. Date: Jun. 5, 2003

(65) Prior Publication Data
US 2005/0003520 A1 Jan. 6, 2005

(30) Foreign Application Priority Data
Nov. 29, 2001 (GR) .............................. 20010100550

(51) Int. Cl.
*H01L 21/00* (2006.01)
*G02B 6/00* (2006.01)
(52) U.S. Cl. .................. 438/31; 438/49; 257/E21.598; 385/12
(58) Field of Classification Search ................. 385/12; 438/1, 29, 31, 49, 99
See application file for complete search history.

(56) References Cited

U.S. PATENT DOCUMENTS
4,791,005 A * 12/1988 Becker et al. ......... 427/255.29
(Continued)

FOREIGN PATENT DOCUMENTS
EP 0 346 016 A2 6/1989
(Continued)

OTHER PUBLICATIONS
Wolf & Tauber. Silicon Processing for the VLSI Era: vol. 1—Process Technology. Lattice Press: Sunset Beach, California. 1986. pp. 182-191.*
(Continued)

*Primary Examiner*—B. William Baumeister
*Assistant Examiner*—Matthew W. Such
(74) *Attorney, Agent, or Firm*—Mathews, Sheperd, McKay & Bruneau, P.A.

(57) ABSTRACT

An integrated optoelectronic silicon biosensor that can detect biomolecules by the change of the optical coupling between the integrated light source and the integrated detector that is caused by the binding of the appropriately labeled analytes onto the recognition molecules, that have been previously immobilized onto the integrated optical fiber that connects the optical source with the detector. The device contains the optoelectronic silicon chip and its biological activation. The optoelectronic chip is realized following integrated circuits fabrication methods so as the light source, the detector and the optical fiber, that optically couples the light source with the detector, to be monolithically integrated on the same silicon substrate. The biological activation of the chip is performed through physicochemical modification of the chip surface in order to permit immobilization of the recognition biomolecules onto the optical fiber surface. The biomolecules to be determined (proteins or oligonucleotides) are labeled with chromophore groups or nanoparticles or enzymes and after their coupling by the recognition biomolecules reduce the optical coupling between the light source and the detector providing a measure of their concentration.

15 Claims, 2 Drawing Sheets

U.S. PATENT DOCUMENTS

Figure 1:
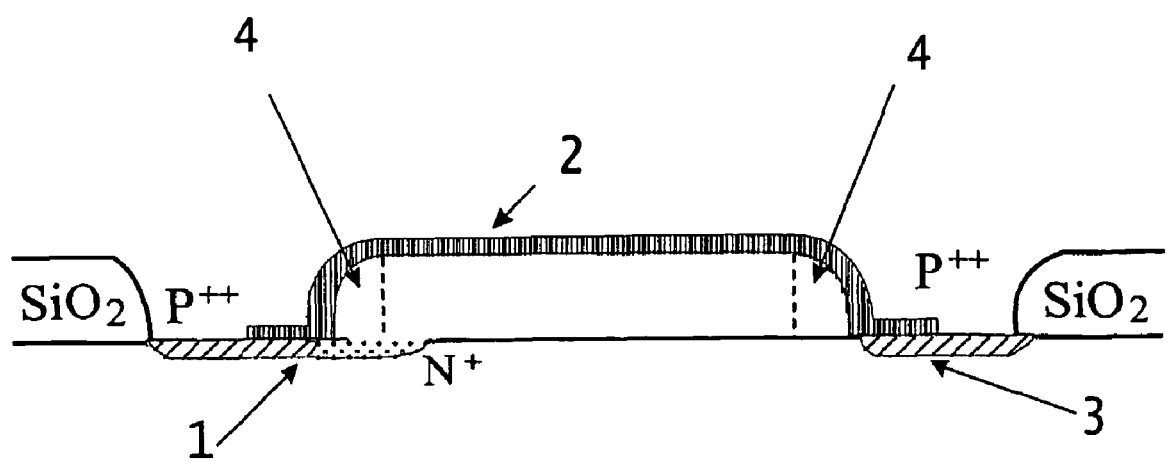

| | | | | |
|---|---|---|---|---|
| 5,418,058 | A | * | 5/1995 | Li et al. .................. 428/327 |
| 5,494,798 | A | * | 2/1996 | Gerdt et al. .................. 435/6 |
| 5,494,801 | A | * | 2/1996 | Bogart et al. ............. 435/7.34 |
| 6,239,017 | B1 | * | 5/2001 | Lou et al. .................. 438/624 |
| 6,342,349 | B1 | * | 1/2002 | Virtanen .................... 435/6 |
| 6,465,241 | B2 | * | 10/2002 | Haronian et al. ........ 435/287.2 |
| 6,589,726 | B1 | * | 7/2003 | Butler et al. .................. 435/4 |
| 6,608,360 | B2 | * | 8/2003 | Starikov et al. ............ 257/481 |
| 6,750,016 | B2 | * | 6/2004 | Mirkin et al. .................. 435/6 |
| 6,801,677 | B1 | * | 10/2004 | Grace et al. .................. 385/12 |
| 2001/0012653 | A1 | * | 8/2001 | Tsukamoto .................. 438/197 |
| 2002/0034756 | A1 | * | 3/2002 | Letsinger et al. .............. 435/6 |
| 2002/0177143 | A1 | * | 11/2002 | Mirkin et al. .................. 435/6 |
| 2002/0182763 | A1 | * | 12/2002 | Stoltz et al. .................. 438/22 |
| 2003/0013218 | A1 | * | 1/2003 | Chason .................... 438/27 |
| 2003/0157731 | A1 | * | 8/2003 | Yguerabide et al. ........ 436/523 |

FOREIGN PATENT DOCUMENTS

| | | |
|---|---|---|
| EP | 725269 A2 * | 8/1996 |
| WO | WO 99/37996 | 1/1999 |
| WO | WO 01/71322 A2 | 9/2001 |

OTHER PUBLICATIONS

Michelle Duval Malinsky, K. Lance Kelly, George C. Schatz and Richard P. Van Duyne. "Chain Length Dependence and Sensing Capabilities of the Localized Surface Plasmon Resonance of Silver Nanoparticles Chemically Modified with Alkanethiol Self-Assembled Monolayers." J. Am. Chem. Soc. 123 (2001): 1471-82.*

Amanda J. Haes and Richard P. Van Duyne. "A Nanoscale Optical Biosensor: Sensitivity and Selectivity of an Approach Based on the Localized Surface Plasmon Resonance Spectroscopy of Triangular Silver Nanoparticles." J. Am. Chem. Soc. 124 (2002): 10596-604.*

Misiakos, K. et al. "Monolithic Integration of Light Emitting Diodes, Detectors and Optical Fibers on a Silicon Wafer: A CMOS Compatible Optical Sensor." IEEE. (1998): 2.2.1-2.2.4.*

Wolf & Tauber. Silicon Processing for the VLSI ERA: vol. 1. Lattice Press, Sunset Beach (1986): pp. 57-58.*

Thompson, M et al., "Biosensors and the Transduction of Molecular Recognition," Analytical Chemistry, vol. 63, No. 7, Apr. 1, 1991, pp. 393A-405A.

Christopoulos, T et al., Chapter 1 "Past, present, and future of immunoassays," Academic Press, Inc.,1996, pp. 1-3.

Burns, M et al., "An Integrated Nanoliter DNA Analysis Device,", Oct. 16, 1998, vol. 282, Science, pp. 484-487.

Victor, S et al., "A Pporous Silicon-Based Optical Interferometric Biosensor," Oct. 31, 1997, Science, pp. 840-843.

Wiki, M et al., "Novel integrated optical sensor based on a grating coupler triplet," 1998, Elsevier Science S.A., pp. 1181-1185.

Caillat, P et al., "Biochips on CMOS: an active matrix address array for DNA analysis," 1999 Elsevier Science S.a., pp. 154-162.

Borrebaeck, Carl A.K., "Antibodies in diagnostics-from immunoassays to protein chips," Immunology Today, vol. 21, No. 8, pp. 379-382.

Chynoweth, A G et al., "Photon Emission from Avalanche Breakdown in Silicon," Phsical Review, vol. 102, No. 2, Apr. 15, 1956, pp. 369-376.

Takahiko, N et al., "Single-chip Integration of Light-Emitting Diode Waveguide and Micromirrors," Jpn. J. Appl. Phys. vol. 34 (1995) pp. 1282-1285, Part 1, No. 2B, Feb. 1995.

Misiakos, K et al., "Monolithic Integration of Light Emitting Diodes, Detectors an Optical Fibers on a Silicon Wafer: A CMOS Compatible Optical Sensor," 1998 IEEE, no page numbers.

Misiakos, K et al., "Monolithic Silison Optoelectronic Biochips," 2001 IEEE, pp. 359-362.

Huang, F. S et al., "Rapid Thermal Annealing of the Through-Film Silicon Implantation on GaAs," Nuclear Instruments and Methods in Physics Research B59/60 (1991) 1003-1006, North-Holland.

* cited by examiner

INTEGRATED OPTOELECTRONIC SILICON BIOSENSOR FOR THE DETECTION OF BIOMOLECULES LABELED WITH CHROMOPHORE GROUPS OR NANOPARTICLES

The invention refers to a monolithically integrated optoelectronic silicon biosensor that can detect biomolecules from the change of the optical coupling between the integrated light source and the integrated detector that is caused by the coupling of appropriately labeled biomolecules to be analyzed on the recognition-molecules which have been previously immobilized onto the optical fiber that connects the light source with the detector.

Biosensors are distinguished in: a) biocatalytic sensors in which an enzyme recognizes the substance to be analyzed (analyte) yielding to products via catalytic reaction and b) sensors of biological affinity, which are further distinguished in immunosensors and DNA sensors, to which an antibody recognize an antigen or a DNA chain fragment recognize the complementary chain fragment, respectively. Based on the transduction mode of the signal produced from the molecular recognition, biosensors can be distinguished in electrochemical, semiconductor, piezoelectric, and optical sensors [1-2].

The protein or oligonucleotide biosensors are usually realized onto solid supports (glass, quartz, polymer, semiconductor materials) on which the recognition biomolecule or more than one biomolecules, each one at a different position, are immobilized. The deposition of biomolecules is performed either directly with microsyringes or printing machines, or with photochemical techniques that combine photolithography and removal of photosensitive protective chemical groups from selected areas. Substrate selection is based on its functionality and cost. Glass and polymer substrates are relatively cheap materials. In addition, some polymers have an innate ability to couple biomolecules. Quartz is more expensive but it has lower autofluorescence and higher transparency in ultra violet light, two characteristics that increase the sensitivity of optical measurements. Silicon substrates can also be used in order to get benefit from the added value of integration of detectors and reading electronics onto the chip with the immobilized biomolecules. In some cases, different materials can be combined with mounting techniques that permit the creation of microchannels for circulation of liquid reagents and sample.

Considering the production and transduction of the measured signal there are several types of biosensors. The majority can be distinguished in two categories: electrochemical and optical devices. Optical devices are the most flexible and allow the simultaneous precise determination of many different analytes in combination with the respective arrays of immobilized molecules. Optical biosensors can incorporate symbolometric devices, grating couplers and devices for absorbance or fluorescence measurement. The ability of optical biosensors to determine accurately many different analytes simultaneously render them the exclusive choice in development of protein or oligonucleotide chips.

The optical biosensors pose, however, the difficulty of monolithically integrating the excitation light source and the detector with the immobilized recognition biomolecules onto the same substrate. So far, the excisting biomolecular detection devices use external light sources not integrated with the biomolecules substrate [3-7]. This demands the use of external light source that increases the packaging requirements making difficult the assembly of the system, requires precise alignment of the light source to the biosensor active elements, increases the volume of the system, and moves away the portability objective.

The present invention solves this problem through the construction of an integrated optoelectronic biosensor that can detect biomolecules due to a change (drop) of optical coupling between the integrated light source and the integrated detector that is caused from the binding of the appropriately labeled biomolecules to be analyzed on the recognition molecules that have been previously immobilized onto the optical fiber that connects the light source with the detector. The set-up includes the optoelectronic silicon chip and its biological activation. The optoelectronic chip is realized following methods for integrated circuit fabrication so that the light source, the detector and the optical fiber, through which the optical coupling of the light source with the detector is performed, to be monolithically integrated on the same silicon substrate. The light is emitted from silicon avalanche diodes reverse biased beyond the breakdown voltage. [8]. The biological activation is performed through physicochemical modification of the chip surface that permits coupling of the recognition biomolecules onto the optical fiber surface. The biomolecules to be analyzed (protein or oligonucleotides) are labeled with chromophores of nanoparticles and after their binding to the recognition molecules decrease the optical coupling between the light source and the detector providing a measure of their concentration.

The innovation of the proposed biosensor relies on the monolithic integration of light sources and detectors along with optical fibers onto which the recognition molecules been immobilized. The molecules to be analysed should have been labeled with chromophore groups or nanoparticles prior to the binding onto the recognition molecules. The optical fiber is self-aligned with the light emitter and the detector using methods for integrated circuit manufacturing. The monolithic integration solves the manufacturing problems concerning the optical connection of the individual optical components and improves the optical coupling compared with other integration methods, for example microassembly of light emitters from synthetic emitters onto silicon substrate [9]. Although the silicon avalanche diodes when used as light emitters have low quantum efficiency, the high coefficient of optical coupling and the high stability of the particular light source guarantee acceptable photocurrents and highly repeatable and stable readings. In addition, it permits, small area detectors with all the commensurate gains in reduced capacitance, small leakage current, and better noise performance. The small area advantage applies also to the light emitter by the very nature of the avalanche diode high field space charge region. Therefore, in terms of space requirements, the basic transducer unit is only limited by the length of the fiber in the waveguiding direction. This opens the opportunity of integration of multiple sensor elements onto one chip, each with a different recognition specificity in a hand held configuration. Had an external light source been used, the multi-analyte aspect could not have been realized in portable arrangements. Finally, the small size of the basic opto-electronic transducer facilitates the stacking of the fluidic module and the entire packaging along with the readout electronics chips in a portable configuration.

The size issue is of critical importance in portable devices. At the same time size is closely connected with the power consumption and endurance attribute of the analyser. In a multianalyte device the active area of every sensing element could be very small, especially in DNA chips. If an external source is to be used a small fraction of the incoming light will excite the sensing element and, therefore, higher optical and electric power will be required. If a focused laser source is employed, the precise alignment of the disposal chip sensor with the light beam will be a major problem in field conditions.

FIG. 1 shows the basic optically interconnected device that consists from the light emitter (1) on the left side, the detector on the right side (3) and the silicon nitride optical fiber in between (2). The detectors (3) are standard p/n junctions optically coupled to the light emitters (1) through the silicon nitride waveguides (2). Good optical coupling is achieved by the self-alignment of the optical fiber (2) with the light emitter (1) and the detector (3) and the way the fiber bends from the field oxide to the end-points of the optical link (4). Since the light emitter and the detector are planar devices, efficient coupling to them is achieved by the bending of the optical fiber (4) so that to contacts both devices under a normal angle. Because a small radius curvature on an optical fiber can cause substantial losses of light, silicon dioxide spacers are at created at the emmiting and receiving ends to minimize the losses. These spacers (4) are created by deposition of oxide (1-2 microns thick) under conditions of low vapor pressure on top of already deposited thermal field oxide. After lithographic patterning, the vertical edges are created by anisotropic etching. Afterwards, an additional deposition of thick dioxide followed by anisotropic etching creates the spacers. An overall, field oxide thickness of 2.5-3 microns of remaining dioxide assures relatively smooth bending and enough distance between the long horizontal segmant of the fiber and silicon interface to minimize substrate losses. The spacers (4) that permit smooth bending of the fiber and part of the field oxide are deposited through sequential chemical vapors depositions (LPCVD) each one followed by annealing at higher temperatures (900° C. for 20 min). This process provides a film with low internal tension thus avoiding cracks.

On top of this dioxide, the optical fiber (2) is lithographically created by deposition of a thin film of Silicon Nitride. The light emitting component of the avalanche diode is created by implanting ions, boron in FIG. 1 where the substrate is of N type, in the silicon nitride film of the fiber with such a power that the higher concentration of the ions to be located between the nitride and the silicon interface. This way the vertical segment of the fiber and the spacers mask the underlying silicon and thus, the avalanche junction lies exactly under this segment. The accurate position requires Rapid Thermal Annealing of the implanted ions (1000° C. for 20 sec). The base of the avalanche diode has been already implanted with complementary ion, phosphorus or arsenate, before the deposition of the spacers. The light emitted towards and within a critical angle of the up-going vertical segment is trapped within the fiber and waveguided all the way to the detector. There, the abrupt breaking of the fiber at the vertical segment/silicon interface assures effective detection even for small diode lengths (as opposed to leaky mode detection). The manufacturing process of the integrated optoelectronic device has many common points with the reference [10] with two major differences:

a. Rapid Thermal Annealing of the implanted ions during the construction of the avalanche diode emitter in order to avoid ions diffusion for the accurate positioning of the junction under the fiber. This way a 10% (absolute) increase in the optical coupling was achieved.

b. The spacers for the smooth bending of the fiber and part of the field oxide are deposited by sequential chemical vapors depositions (LPCVD) each one followed by annealing at higher temperature from the deposition temperature providing a film with low internal tensions that is not prone to cracking thus, reducing the percentage of broken optical fibers and improving the stability of the optical coupling.

An important element of the present invention is the successful immobilization of recognition biomolecules (antibodies, antigens, oligonucleotides) onto the optical fiber surface (of the silicon chip). The immobilization of biomolecules on the surface of silicon nitride requires its modification with aminosilanes or thiosilanes or with the creation of thin polymer films. In all cases, however, for the successful modification of the surface its previous cleaning and/or hydrophilization is required. This is achieved by treating the surface with solutions of strong acids in combination with oxidizing agents e.g. mixture of sulfuric acid and hydrogen peroxide (Piranha). These methods are appropriate for the hydrophilization of silicon nitride but they cannot be applied in the case of the biosensor described here since they destroy the aluminum contacts that are necessary for biosensor operation.

In the present invention a method for cleaning and hydrophilization of the silicon nitride surface with oxygen plasma is included. Hydrophilization is followed by modification of the surface through immersion of the wafer in solution of aminosilane or thiosilane or creation of thin polymer film with spin coating. Using appropriate reagents is possible to immobilize the recognition biomolecules onto the surface of the optical fiber by covalent coupling as well as by adsorption.

The creation of measurable signal is based on the fact that the analyte molecules after their coupling on the recognition elements that exist on the optical fiber change the coefficient of optical coupling between the light source and the detector. This change is measured as an alteration in the detector photocurrent. The interaction of the immobilized analyte molecules (oligonucleotides or proteins) with the waveguided photons is accomplished through physics of evanescent wave optics. In order to enhance this interaction, chromophore groups or special nanoparticles that are efficient photons couplers are used for labeling of analyte molecules. The chromophore groups absorb photons through transitions on their electronic structure. Nanoparticles are more efficient concerning the reduction of the optical coupling either due to increased photon scattering or due to strong resonance of surface plasmons. This resonance is particularly strong in gold nanoparticles. In this case, the resonance can be further enhanced by metal deposition on the gold nanoparticles surface, after their immobilization that will increase significantly their size. Metal deposition is usually achieved from a metal ion solution in presence of a reducing agent. In all cases, the measurable signal is the percentage of light drop before and after the binding of the labeled analyte molecules. The drop is expressed as the ratio of photocurrent measured before the binding of the labeled molecules towards the photocurrent before their binding.

Except for the chromophore groups or the nanoparticles there is the potential of use biomolecules labeled with enzymes in combination with chromogenic substrates that provide an insoluble product (precipitate). The deposition of precipitate microparticles onto the surface of the optical fiber decrease the optical coupling of the emitter with the detector due to increased photon scattering, which result in significant drop of the photocurrent that is measured by the detector. In this case, the measurement is performed in presence of chomogenic substrate solution and thus, care should be taken in order that the aluminum contacts of the microdevice to be isolated from the optical fiber(s). Enzyme, commonly used in immunoassays, such as the horse radish peroxidase (HRP) in combination with several chromogenic substrates that yield insoluble products (e.g. 4-chloro-1-naphthol, 3,3',5,5'-tetramethyl-benzidine) and alkaline phosphatase (AP) in combination with 5-bromo-4-chloro-3-indole phosphate and blue of p-nitrotetrazole (BCIP/NBT), can be used for labeling of the biomolecules.

EXAMPLE 1

Figure 2:
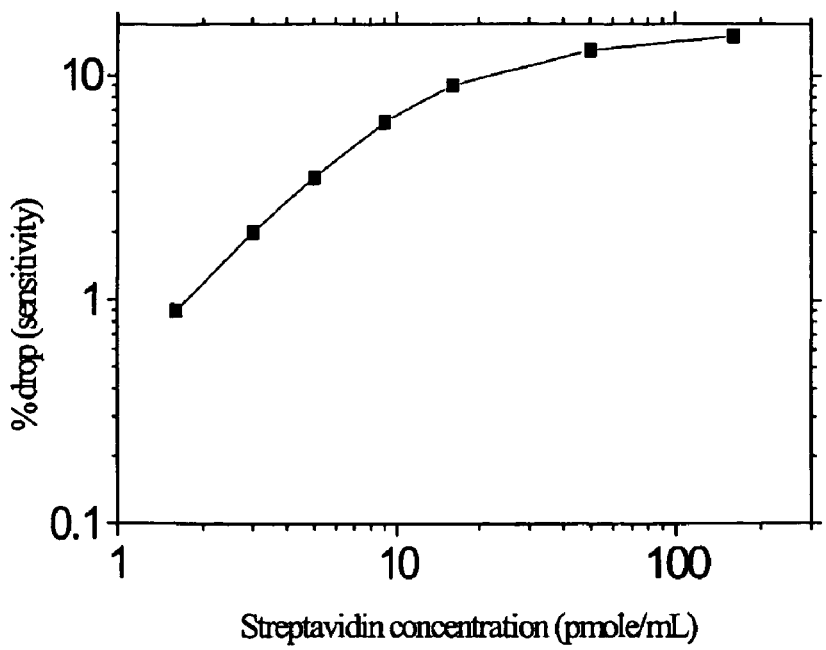

The die with the device of FIG. 1, which has been fabricated as described in page 3, line 10, to page 4, line 9, is cleaned and hydrophilized in oxygen plasma for 30 seconds. Following that, the device is immersed in a 2% (v/v) 3-amino-propyltriethoxysilane solution in doubly distilled water for 20 min. Then, the device is immersed in deionized water for 45 seconds and the water that remains on the surface is removed under a gentle nitrogen stream. After that, the wafer is placed on top of a heating plate adjusted at 120° C. for 20 minutes. Then, on top of the optoelectronic microdevices presented in FIG. 1, a 1 mg/mL solution of 6-((biotinyl)amino)hexanoic acid sulfosuccinimidyl ester in 0.1 M carbonate buffer, pH 8.5 is placed using a micropipette. After a 1-h incubation, the wafer is washed with deionized water and covered with blocking solution (10 g of bovine serum albumin in 0.1 M carbonate buffer, pH 8.5) for 30 minutes in order to cover the free binding sites of the solid surface. Respective dies prepared following all the stages described above with the difference that they were not biotinylated are used as blanks. After that, the modified with biomolecules dies are washed with deionized water, dried under nitrogen stream and the photocurrent of the detectors before the addition of the analyte is determined. After the measurement, solutions of streptavidin labeled with R-Phycoerythrin at concentrations ranging from 1.66 to 166 pmole/mL in 0.05 M phosphate buffer, pH 6.5, which contains 40 g of bovine serum albumin, 9 g of sodium chloride and 0.5 g of sodium azide per liter, are placed on the devices and incubated for 30 min. The devices are, then, washed with 0.05 M phosphate buffer, pH 6.5, containing 0.5 mL of Tween 20 per liter, with deionized water and dried under nitrogen stream. The detector photocurrent is measured. The R-phycoerythrin molecules, that are immobilized onto the optic fiber, act as chromophors and absorb waveguided photons in the region of blue and green light. The streptavidin detection sensitivity curve obtained using optoelectronic devices of FIG. 1 with a 900-micron long optical fiber is presented in FIG. 2. As it is calculated, the detection limit is 1.6 pmole/mL.

EXAMPLE 2

Figure 3:
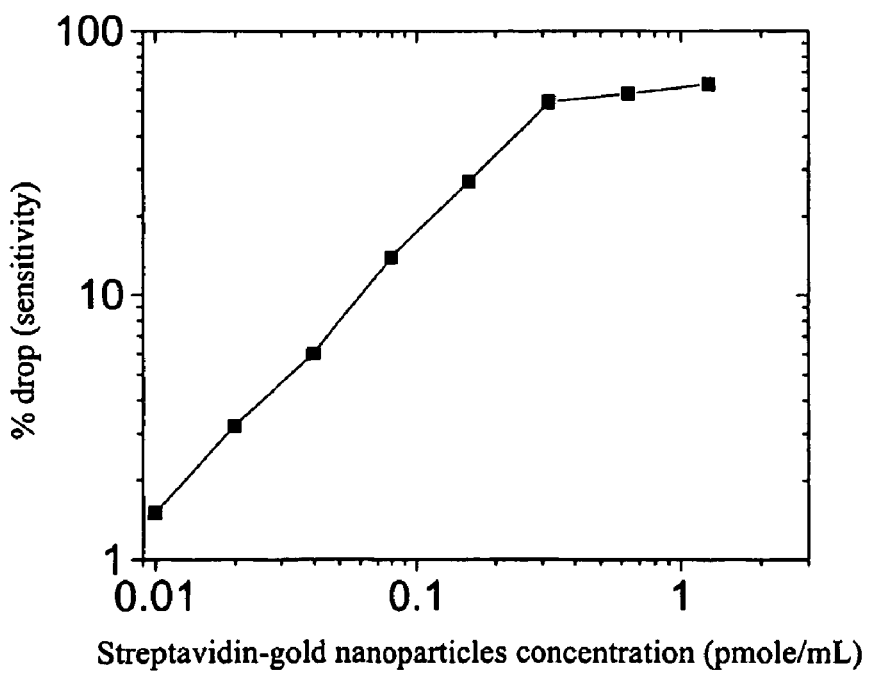

On the die with the device of FIG. 1, which has been fabricated as described in page 3, line 10, to page 4, line 9, after immobilization on its surface of biotin molecules, coverage of the free binding sites of the solid support and measurement of the detection photocurrent, according to the method of the example 1, solution of streptavidin labeled with gold nanoparticles of 8 nanometer in diameter at concentration of 0.01-1.26 pmole/mL in 0.05 M tris(hydroxyamino)methane-hydrochloric acid buffer, pH 7.4, which contains 5 g of bovine serum albumin, 9 g of sodium chloride, 0.5 g of sodium azide, and 0.5 mL of Tween 20 per liter, are added using a micropipette. After incubation for 30 minutes, the dies are washed firstly with 0.05 M tris(hydroxyamino)methane-hydrochloric acid buffer, pH 7.4, which contains 0.5 mL of Tween 20 per liter, and then with deionized water. After that, the wafers are dried under nitrogen streamand the detector photocurrent is measured. The nanoparticles that have been immobilized onto the optical fibers exhibited strong surface plasmon resonance and due to this phenomenon they provide a sensitivity curve (FIG. 3) with a detection limit of 8 fmole/mL, for the optoelectronic device presented in FIG. 1 using the 900-micron long optical fiber.

EXAMPLE 3

On the die with the device of FIG. 1, which has been fabricated as described in page 3, line 10, to page 4, line 9, which has been treated following the process that is described in example 2, a solution for metal silver deposition that contains 0.11 g of silver lactate, 0.85 g of hydrocinone in 100 mL of 0.2 M citrate buffer, pH 3.5, is applied for 20 minutes. After that, the wafers are washed with deionized water and dried under nitrogen stream. Measurement of the detectors photocurrents follows. The silver deposition on the already immobilized gold nanoparticles increases significantly their size (the diameter of the nanoparticles is increased from 8 to 100 nanometers) and results in further significant decrease of the measured photocurrent compared with the photocurrent that is measured after binding of biomolecules labeled with gold nanoparticles (e.g. 80% decrease of the signal for a concentration of gold nanoparticle labeled streptavidin of 0.6 femtomoles per mL).

REFERENCES

[1] M. M. Thompson et al., "Biosensors and the transduction of molecular recognition", Anal. Chem., 63, 393 A, 1991.

[2] E. P. Diamandis, T. K. Christopoulos eds, "Immunoassay", San Diego, Academic Press, 1996.

[3] M. A. Burns et al "An Integrated Nanoliter DNA Analysis Device" *Science,* 1998 Oct. 16; 282: 484-487

[4] V. S.-Y. Lin et al "A Porous Silicon-Based Optical Interferometric Biosensor" *Science* 1997 Oct. 31; 278: 840-843.

[5] M. Wiki, R. E. Kunz, G. Voirin, K. Tiefenthaler, A. Bernard "Novel integrated optical sensor based on a grating coupler triplet" *Biosensors and Bioelectronics* (1998) 1181-1185.

[6] P. Caillat et al "Biochips on CMOS: an active matrix address array for DNA analysis" *Sensors and Actuators B* 61 (1999) 154-162

[7] C. A. K. Borrebaeck "Antibodies in Diagnostics—from immunoasaays to protein chips" Review, *Immunology Today,* Vol21, 379, 2000

[8] A. G. Chynoweth and K. G. McKay, "Photon emission from avalanche breakdown in silicon", *Phys. Rev.,* 102, 369-376, 1956

[9] Takahiko Nagada et al. "Single-Chip Integration of Light-Emmiting Diode, Waveguide and Micromirrors", *Japanese Journal of Applied Physics*, Vol. 34, 1282 1285, 1995

[10] K. Misiakos, E. Tsoi, E. Halmagean, S. Kakabakos, "Monolithic integration of light emitting diodes, detectors and optical fibers on a silicon wafer: a CMOS compatible optical sensor", *International Electron Devices Meeting* 1998, San Francisco, Calif., Dec. 9, 1998.

The invention claimed is:

1. A method of making an integrated optoelectronic sensor, the sensor comprising
an avalanche diode light source (1),
a silicon nitride optical fiber (2) formed from a silicon nitride film, wherein the light source is self-aligned to the optical fiber via implanting ions through the silicon nitride film,
a detector (3), and
spacers (4) for the smooth bending of the fiber;
wherein the method comprises
depositing the spacers and part of a field oxide through sequential chemical vapor deposition (LPCVD), each deposition followed by annealing at an annealing temperature that is higher than the deposition temperature in order to ensure the creation of an oxide film with low internal tensions and avoid cracking.

2. The method of claim 1 wherein the annealing is performed at 900° C. for 20 minutes.

3. The method of claim 1 further comprising immobilizing recognition molecules on the sensor by a procedure comprising: hydrophilization of the optical fiber in oxygen plasma, immersion of the optical fiber in an aminosilane solution, drying of the optical fiber and subsequent immersion of the optical fiber in a solution of biomolecules.

4. The method as in claim 3 wherein the sensor is fabricated on a substrate and has more than one set of light source (1)/optical fiber (2)/detector (3) integrated on the same substrate, each set having a different biomolecule on the fiber (2).

5. A method for the measurement of analyte concentration measured with a sensor made by the method of claim 1, comprising binding analyte biomolecules to recognition biomolecules immobilized on the sensor and detecting photocurrent at the detector, the measurement being expressed as a ratio of the photocurrent after the analyte binding relative to the photocurrent prior to the analyte binding.

6. The method of claim 5 wherein the analyte biomolecules are labeled with chromophore groups that present strong optical absorption.

7. The method of claim 5 wherein the analyte biomolecules are labeled with nanoparticles that present strong optical scattering or strong surface plasmon resonance.

8. The method as in claim 7, wherein, after the binding of the analyte biomolecules labeled with nanoparticles, a solution for depositing a metal is added to increase the size of the nanoparticles.

9. The method as in claim 7, wherein, after the binding of the analyte biomolecules labeled with nanoparticles, chemicals for depositing liquid metal are added to increase the size of the nanoparticles.

10. The method as in claim 5, wherein the analyte biomolecules are labeled with enzymes and the method further comprises adding a chromogenic substrate that on contact with the enzyme yields insoluble product which precipitates onto the optical fiber surface causing strong optical scattering.

11. The method of claim 1, further comprising a procedure for immobilizing recognition molecules on the sensor, comprising: hydrophilization of the optical fiber in oxygen plasma, immersion of the optical fiber in an aminosilane solution, drying of the optical fiber and subsequent immersion of the optical fiber in a solution of biomolecules.

12. A method for the measurement of analyte concentration comprising binding analyte biomolecules to immobilized recognition biomolecules, and detecting photocurrent at a detector of a sensor made by the method of claim 1, the measurement being expressed as a ratio of the photocurrent after the analyte binding relative to the photocurrent prior to the analyte binding.

13. A method of making an integrated optoelectronic sensor, the sensor comprising
a silicon nitride optical fiber (2) formed from a silicon nitride film,
an avalanche diode light source (1) that is self-aligned with the optical fiber (2),
a detector (3), and spacers (4) for the smooth bending of the fiber, the spacers and part of a field oxide being deposited through sequential chemical vapors depositions (LPCVD) wherein the method comprises
forming the avalanche diode light source (1) by ion implanting through the silicon nitride film and rapid thermal annealing, wherein the rapid thermal annealing takes place at 1000° C. for 20 seconds.

14. The method as claimed in claim 1, further comprising performing individual sequential chemical vapor deposition and annealing steps, wherein each of the individual deposition steps of said chemical vapor depositions (LPCVD) of the spacers and part of the field oxide is followed by an annealing step at a temperature that is higher in comparison to the deposition temperature in order to ensure the creation of a film with low internal tensions and avoid cracking.

15. The method of claim 14 wherein the annealing of the spacers and part of the field oxide is performed at 900° C. for 20 minutes.

* * * * *